(12) United States Patent
Besselink

(10) Patent No.: US 11,318,017 B2
(45) Date of Patent: May 3, 2022

(54) STENTED VALVE

(71) Applicant: Petrus A. Besselink, Enschede (NL)

(72) Inventor: Petrus A. Besselink, Enschede (NL)

(73) Assignee: Petrus A. Besselink, Enschede (NL)

( * ) Notice: Subject to any disclaimer, the term of this patent is extended or adjusted under 35 U.S.C. 154(b) by 101 days.

(21) Appl. No.: 16/489,528

(22) PCT Filed: Feb. 27, 2018

(86) PCT No.: PCT/IB2018/000257
§ 371 (c)(1),
(2) Date: Aug. 28, 2019

(87) PCT Pub. No.: WO2018/158635
PCT Pub. Date: Sep. 7, 2018

(65) Prior Publication Data
US 2020/0000593 A1    Jan. 2, 2020

Related U.S. Application Data

(60) Provisional application No. 62/464,719, filed on Feb. 28, 2017.

(51) Int. Cl.
*A61F 2/24*    (2006.01)
(52) U.S. Cl.
CPC .......... *A61F 2/2469* (2013.01); *A61F 2/2418* (2013.01); *A61F 2/2433* (2013.01);
(Continued)
(58) Field of Classification Search
CPC ............................ A61F 2/2469; A61F 2/2418
See application file for complete search history.

(56) References Cited

U.S. PATENT DOCUMENTS 6,726,715 B2 * 4/2004 Sutherland ............ A61F 2/2412
623/2.1
8,628,571 B1    1/2014 Hacohen et al.
(Continued)

FOREIGN PATENT DOCUMENTS

| EP | 1472996 A1 | 11/2004 |
|---|---|---|
| WO | 2011159779 A2 | 12/2011 |
| WO | 2015184450 A1 | 12/2015 |

OTHER PUBLICATIONS

International Search Report and Written Opinion dated Jul. 25, 2018 in related International Application No. PCT/IB2018/000257.
(Continued)

*Primary Examiner* — Brian A Dukert
(74) *Attorney, Agent, or Firm* — Thomas E. Lees, LLC

(57) ABSTRACT

A stented valve suitable for use in body ducts. The valve includes an expandable support structure and an attached flexible membrane that changes shape when the valve opens and closes. The expandable support structure has the shape of a stent with a series of interconnected expandable unit cells and elongated support beams. When the valve is open, body fluid can flow around the membrane and pass through the gap between it and the inner stent surface. In one configuration, a set of two valves is combined with an intermediate inflatable balloon to create a cardiac assist pumping device. In another embodiment, valve closure can be achieved by remotely controlled valve leaflets actuation. A double aorta valve frame is used to accommodate shape and diameter variations of the annulus in an outer valve frame, while the inner valve frame has dimensions for optimized performance of the valve membrane.

21 Claims, 7 Drawing Sheets

(52) U.S. Cl.
    CPC .... *A61F 2/2436* (2013.01); *A61F 2220/0016* (2013.01); *A61F 2230/0067* (2013.01); *A61F 2230/0069* (2013.01); *A61F 2250/0039* (2013.01); *A61F 2250/0067* (2013.01)

(56) References Cited

U.S. PATENT DOCUMENTS

| | | | | |
|---|---|---|---|---|
| 9,839,511 | B2 * | 12/2017 | Ma | A61F 2/2412 |
| 9,901,444 | B2 * | 2/2018 | Valdez | A61F 2/2412 |
| 2010/0256752 | A1 * | 10/2010 | Forster | A61F 2/2418 623/2.17 |

OTHER PUBLICATIONS

International Preliminary Report on Patentability dated Feb. 1, 2019 in related International Application No. PCT/IB2018/000257.

* cited by examiner

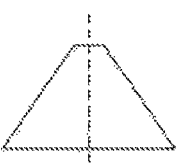
Fig. 4a
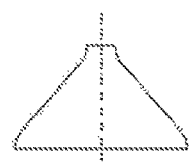
Fig. 4b
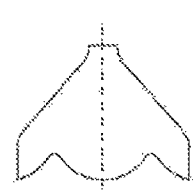
Fig. 4c
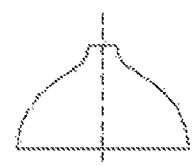
Fig. 4d
Fig. 7
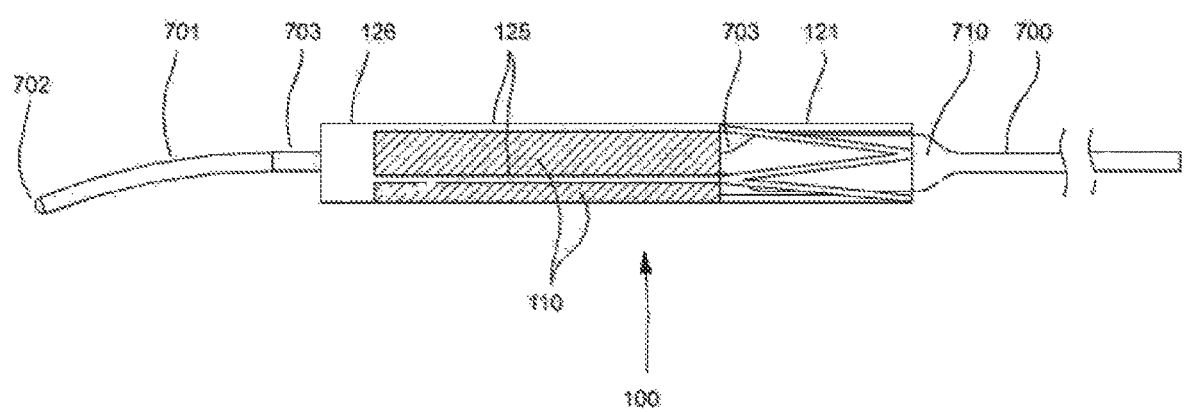

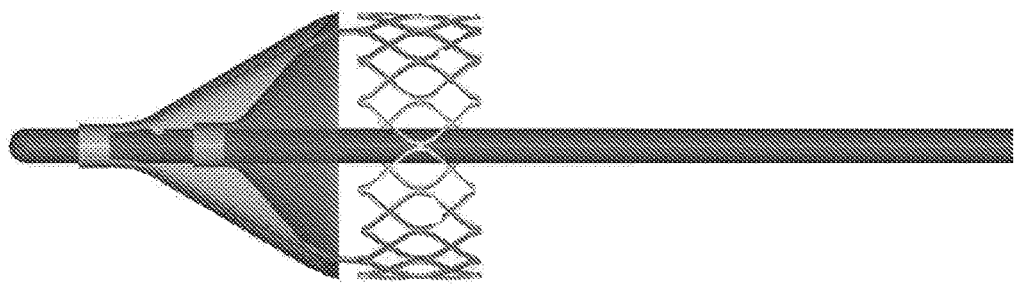
Fig. 13a
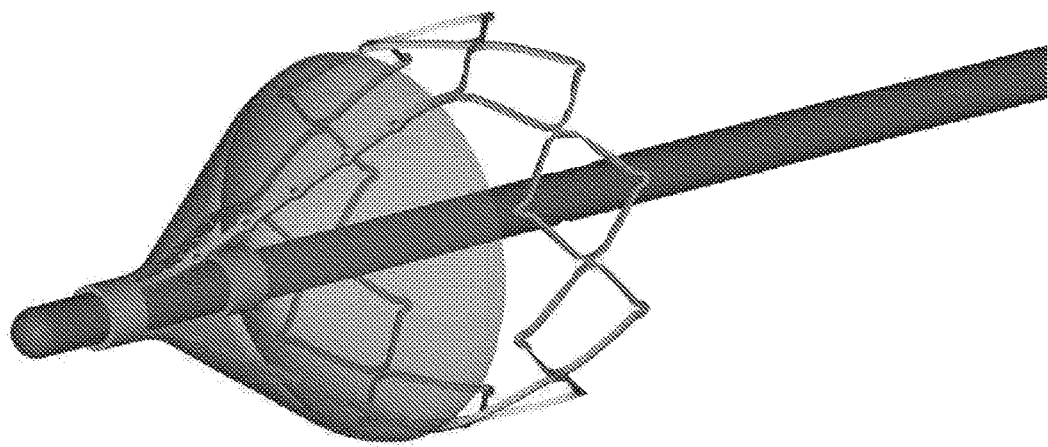
Fig. 13b
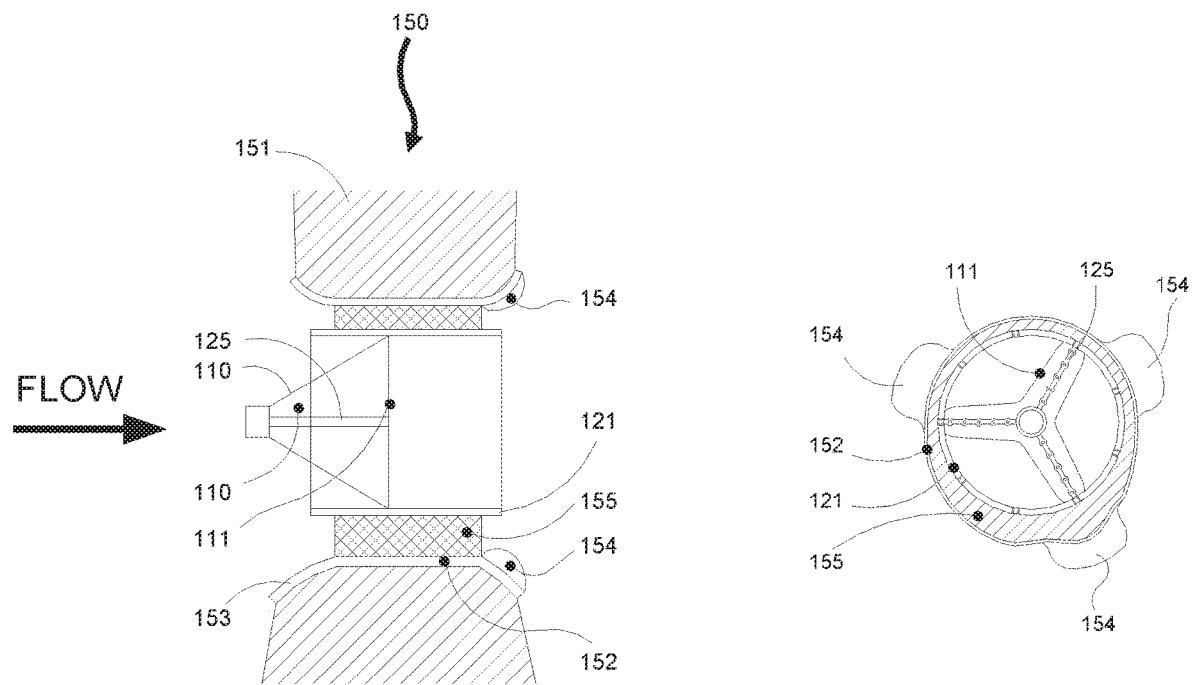
Fig. 14a
Fig. 14b

STENTED VALVE

CROSS-REFERENCE TO RELATED APPLICATIONS

This application claims the benefit of U.S. Provisional Application Ser. No. 62/464,719, filed Feb. 28, 2017.

BACKGROUND

This disclosure relates to the field of producing an improved valve, which can be used in veins, arteries and other body ducts.

In natural valves cells that are connected to the duct wall generally develop the flexible valve membranes. This is logical, because if there were no connection to the wall, the membrane would not receive the necessary elements, building materials and nutrition to grow and maintain its properties during lifetime. Further a valve membrane would float away with the body fluid if it were not directly connected to the wall. Consequently, in natural body valves the fluid will always flow through the aperture that opens up when the membrane takes its open position. This means that the main flow basically is centered in the body duct and that the deforming valve membrane is plied against or nearer to the wall.

Prosthetic valves can be implanted by means of surgery or by minimal invasive techniques using catheter-like devices.

In the first category there are several mechanical systems with a more rigid moving part, like a ball valve or rotating hinged plates. Examples of these devices are single and double flap designs, manufactured by companies as Abbott, Medtronic, Sulzer, Liva Nova and others. Some of the main disadvantages of these devices are a need for permanent treatment of anticoagulants, noisy operation, and a need for a large-scale operation to implant.

Deformable valve materials form another category. There is a wide range of biologically based valves made of natural valves or composed of biological materials such as percardial tissue. Well-known companies such as Edwards Lifesciences, Medtronic, Sulzer, Liva Nova and others too market these.

Polymer valves are new and several companies are in the process of developing such products. A polymer for such valves could be the well-known polyurethane.

Such prosthetic valves are generally making use of a support frame and the flexible membrane that works as the actual deforming valve. In these valves the membrane is directly connected at the annular base and struts to the supporting frame by stitching, gluing, dipping, welding etc. This also means that the flow is not directly guided along the inner surface of the supporting frame, but merely through the center of the duct. In some cases the covered inner surface of the support frame has the risk of closing the entrance of side lumens, for example a coronary artery which descends from the aorta. This means that accurate placement is very critical.

The construction with a membrane directly connected to the support frame also creates the risk of zones, where the blood flow is not smooth enough, which may cause thrombosis and/or platelet deposition. Such problems should be avoided by making an appropriate design, in which the body fluids can easily flush around all valve parts, avoiding too much turbulence or dead zones with no or not enough flow.

U.S. 20030114913 discloses a valve prosthesis, which can be delivered by means of a balloon catheter. The flexible valve membrane is located inside a balloon expandable stent ring and attached thereto by means of stitches. The valve tissue is at the same axial location as the supporting stent frame.

Examples of similar designs with the valve placed inside a self-expandable or balloon-expandable stent are disclosed in numerous patents, for example U.S. Pat. Nos. 6,503,272; 6,458,153; 6,027,525; 5,957,949 and 5,855,601.

In the case of a balloon expandable stent, the delivery balloon, mounted near the distal end of a long catheter, is essentially placed inside the stent frame and thus also inside the same area where the folded membrane is located. This causes a pile up of several materials, all adding to the insertion profile of the device. The stent and all materials inside it are crimped as much as possible on the catheter, but this is limited by the minimal required thickness of stent struts, membrane, balloon material and catheter core. Damage to the membrane must be avoided, so crimping forces should be limited as well. Also the radial pressure that is exerted to the membrane, while the balloon is inflated to expand the stent, may cause damage to the fragile membrane material. In fact the membrane is squeezed between the balloon and the inner stent wall.

In other devices, like for example the one disclosed in U.S. 20020188348 the valve is not situated inside the supporting frame. Here the support frame has elongated struts, which are covered with a series of valve leafs. The elongated struts move together with the attached valve leafs when the valve opens and closes. In this design, like in the previous ones, the blood flow always goes through the center part of the valve.

In general, if a valve opens in the center, while the flaps are moving outside, the cross section that allows blood flow is determined by the total surface area that the cross section of the support frame, inside layer covering the support structure plus valve flaps occupy. Suppose that the open valve has a circular opening and that in an open state the valve flap tips move from the center over a maximum distance of half the body lumen radius. They would than give only a circular area with half the body lumen diameter free. In such a case only 25% of the total surface area of the body lumen is then open.

However, this means that 75% of the surface area is not available for blood flow. It would therefore be better to use a valve, which does not open in the center, but instead allows the blood to flow around it. With the same movement of the valve flap tips over half the radius, but now with flaps moving from the body lumen wall inward, the effective surface area becomes 75% instead of 25%. Therefore it may be better to design valves that allow the body fluid to flow around them instead of through them.

Another disadvantage of valves with the valve membrane attached to the wall is that during lifetime new cells may grow onto the membrane surface. These cells could grow from the body lumen wall and gradually cover parts of the membrane tissue, or even the entire membrane. This contamination can hinder a proper functioning of the valve or even cause major problems over time.

If the valve membrane was not in direct contact with the body lumen wall the contamination with new growing cells on the membrane tissue is much less likely.

Not only new cells may cause contamination of the heart valve. Another problem is that platelet adhesion and collection of emboli may occur on sites where the flow is very low. This can be caused if there are "dead zones" in the flow pattern. It is therefore essential to design a valve that is automatically kept clean by the blood flow, which can reach the entire valve surface.

SUMMARY

The present disclosure provides a series of new concepts in the field of aortic valves and other human valves. Such valves are suitable for conventional placement by surgery, but especially optimized for the more favorable percutaneous implantation.

It is an object of the disclosure that a stented prosthetic valve comprises a flexible membrane, held in a body duct by means of a support frame, whereby the membrane can collapse in order to allow a flow around it, passing through the openings between the membrane surface and the inner wall of the duct.

Another object of the disclosure is that the valve membrane closes the valve by expanding towards the wall of the duct, instead of valves that open by expansion towards the wall.

Still another object of the disclosure is that the valve membrane movements are caused by a combination of pressure, elasticity of the membrane itself and elasticity of additional elements connected thereto.

It is also an object of the disclosure that the support frame may be placed by surgery or by minimal invasive techniques, comprising the use of a balloon catheter with a balloon expandable frame or by delivery of a self-expanding frame from a sheath, followed by post-dilatation.

Another object of the disclosure is that by a proper dimensioning of the valve membrane a flushing of the membrane surface will automatically keep it clean on all sides.

Still another object of the disclosure is the use of an additional one-way valve in the tip of the device to flush the blood from the membrane surface to prevent contamination and cell adhesion.

It is also an object of the disclosure that the surfaces of the stented prosthetic valve can be treated with one or both of a coating and additional drugs to improve the characteristics or to lower the chance on problems during use.

It is further another object of the disclosure that by variation of the type of stent, the placement can be done by balloon expansion, self-expansion, balloon triggerable self-expansion, balloon expandable light curing stent surfaces and combinations thereof.

It is another object of the disclosure that the flexible membrane of the valve is reinforced with fibers with high tensile strength and high flexibility, and/or that the membrane is given shape control by embedding or connection of elastic fibers or struts.

Another object of the disclosure is that the membrane edges may be bulged or have protuberant edges to improve the sealing characteristics of the membrane when it is pressed against the lumen wall or any layer covering the inside wall of the stent.

It is also an object of the disclosure that the valve is placed either downstream from, upstream from or inside the supporting stent and that more than one valve may be placed.

It is further another object of the disclosure that the flexible membrane may be made of any polymer, metal, organic tissue, fabric or combinations thereof.

Another object of the disclosure is that the stent and the support frame for the flexible membrane are made of metal, polymer, and combinations thereof.

Another object of the disclosure is that the shape and number of struts, supporting and connecting the frame is variable, depending of the use of the valve.

It is also another object of the disclosure that the stent may be provided with hooks to hold it secured in the body lumen.

It is another object of the disclosure that the valve needs less valve movement to reach a certain surface area available to let blood pass.

Another object of the disclosure is that less valve movement at the leaflet folding area will lead to less structural fatigue and failure of the valve membrane material.

Still another object of the disclosure is that the valve holder frame may have flared ends in order to enable a secure fixation in the annulus of the native aortic valve.

Another object of the disclosure is that the moving leaflets of the valve membrane close against a separate polymer skirt or skin that is mounted on the valve holder frame to act as a sealing edge.

It is also an object of the disclosure that the valve edge closes against a separate skirt at a diameter that is smaller than the maximum diameter of the support frame.

It is further another object of the disclosure that the valve leaflets need less movement for creating the same opening surface, compared with valves that open in the center.

It is also an object of the disclosure that the valve construction leads to less structural fatigue and failure of the leaflets, compared with valves that open in the center.

Another object of the disclosure is that one or more valves and their support frames are mounted on a catheter carrying an intra-aortic balloon pump with at least one repeatedly inflatable and deflatable balloon.

Another object of the disclosure is that the two or more one way valves and at least one balloon are combined in any configuration in order to reach effects comprising optimizing the blood flow, limiting whipping by the balloon, keeping the balloon in the center of the aorta, maintaining the axial position of the catheter, limiting energy losses, enabling the use of smaller balloons for the same flow.

It is also an object of the disclosure that an assembly with a first conical valve membrane with a first top angle and a second conical membrane with a second top angle are mounted to the same frame, wherein both membranes are attached to each other at the cone base, thus acting together as an one way valve and wherein the intermediate space enclosed by both membranes is in direct contact with the lumen of the catheter that carries the device, so that raising the pressure in the intermediate space causes closure of the valve independent of the actual pressure difference over the valve caused by the heart beating.

Still another object of the disclosure is that a prosthetic aortic valve is assembled from an inner expandable valve holder frame with valve holder struts and a conical valve membrane connected thereto, an outer annulus holder frame and an adaptive sealing skirt that prevents paravalvular leakage between both frames.

It is also an object of the disclosure that the outer annulus holder frame has a flared end at the upstream side.

It is further another object of the disclosure that the outer annulus holder frame has a flared end at the downstream side.

Another object of the disclosure is that the flared end at the downstream side of the annulus holder frame has a three-lobed shape to accommodate to the anatomy of the aortic sinuses.

Still another object of the disclosure is that the double frame construction with a second surrounding support frame and a valve holder frame is used in other locations in the human body.

Another object of the disclosure is that the amount of cells in tangential and axial directions in the support frames may be varied, dependent on the place of use.

BRIEF DESCRIPTION OF THE DRAWINGS

The following detailed description of the preferred embodiments of the present disclosure can be best understood when read in conjunction with the following drawings, where like structure is indicated with like reference numerals and in which the various components of the drawings are not necessarily illustrated to scale:

FIGS. 4a-4d shows examples of possible embodiments for the flexible membrane.

FIG. 7 shows the device while it is mounted on a delivery catheter.

FIG. 12b shows a detail of the left frame and a part of the balloon of FIG. 12a.

FIGS. 13a and 13b show two views of an inflatable valve, which can be actively closed by raising the internal pressure between the valve leaflets.

FIGS. 14a and 14b show such a valve, built into a double frame, where FIG. 14a gives a side view of such an aortic valve 150, built into the annulus 151, while FIG. 14b shows a cross section of the same, but now in the open state and with the annulus left away for clarity.

DETAILED DESCRIPTION

The advantages of the disclosed device and method will become more apparent after reference to the following description, wherein some embodiments are elucidated.

There are several options to make a valve according to the present disclosure, and the embodiment that is described hereafter is only meant to show the principle.

Figure 1:
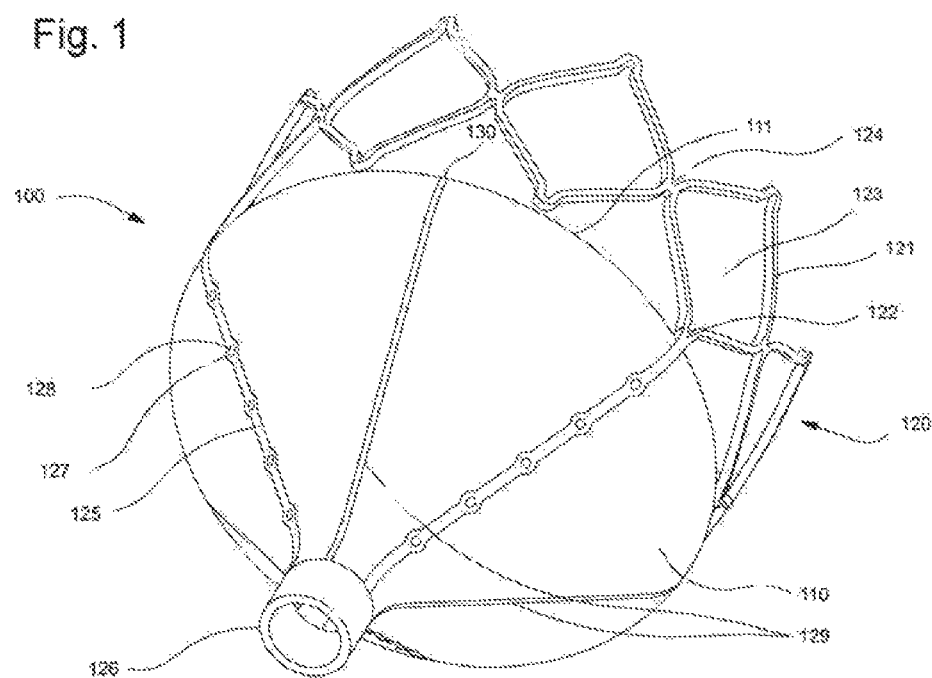
FIG. 1 shows a side view of a support frame for a valve with an expandable stent made of a single row of unit cells, which has elongated valve holding struts that are configured to hold a flexible valve membrane. The membrane is in its expanded state and closes the lumen.

FIG. 1 shows a valve 100, comprising a valve membrane 110 and a support frame 120, made from one row of unit cells, cut out of a piece of tubing. The support frame has a stent section 121 and support struts. The production may be done by for example laser cutting, followed by electropolishing and shape setting of a superelastic or linear elastic Nitinol alloy or a balloon expandable material like stainless steel or any other well-known material for making stents. In principle the stent 121 can be made as a balloon expandable type, a self-expanding type or a balloon triggerable self-expanding (bistable) type. If needed, the support frame 120 may even be made of a different type, but in that case other ways to implant the device may become necessary. This would also be the case if the support frame 120 is made non-deformable, like in the support frames of conventional heart valves. These are normally implanted by surgery techniques.

However, for the coming description of the figures the support stent 121 is shown as an expandable design with a relatively short length, but it may be clear that valves according to this disclosure may be used in combination with longer stents as well. Also the axial position of the valve in relation to the stent may vary in numerous optional embodiments, without departing from the scope of the claims.

The support frame 120 of FIG. 1 has a stent section 121, made of a number of expandable unit cells, and a series of valve supporting struts 125, connected to the stent 121 at connection points 122. If the frame is made from a single piece of tubing, struts 125 are an extension of the stent 121. Stent 121 has 9 unit cells 123, connected to each other at points 124. Three struts 125 are connected to every third unit cell of the stent 121. A tip ring 126 connects the valve supporting struts 125 to each other at a common place. Although a monolithic structure is shown, it will be appreciated that it is also possible to make such a frame by joining several separate components together. In such cases the tip ring would be a separate part, eventually with a diameter that differs from the original tube out of which the support frame was made.

The three elongated support struts 125 act as a frame for the flexible valve membrane 110 and have to keep this membrane in place the entire lifetime. Detachment of the membrane from the struts is unacceptable. Therefore the struts must have a geometry which is adapted to create a secure attachment of the membrane to these struts. As an example, over the length of the struts a series of wider parts 127 can prevent slipping off of the membrane. If a membrane is attached to the struts, for example by a dipping technique in which a polymer layer like polyurethane is created, these wider sections can increase the shear forces and thus the strength of the attachment. The membrane cannot easily be pulled off such struts, because they have a good shape fit. All kinds of geometries can be used to increase the strength of this metal to membrane connection. Eventual additional holes 128 may be cut in the struts to improve the connection. Additional stitches may be attached, using the holes as an anchoring place. In a specific embodiment, additional fibers for shape control or reinforcing fibers may be embedded in the valve membrane, in order to improve its characteristics. The holes in the support struts can then be used for a proper attachment of these reinforcing fibers to the frame. In PCT/IB2003/004070 the technology of reinforcing membranes by means of high strength fibers and/or fibers for shape control is extensively described and claimed by the same inventor. The reinforcement fibers can run in tangential direction, but also in all kinds of other directions, like perpendicular to tangential or all kinds of inclined directions between 0 and 90 degrees from tangential.

In FIG. 1 three elastic struts 129 are running from the connection ring or point 126 at the apex through the membrane 110 to a free end 130 close to the membrane's edge 111. The function of these struts 129 is to help to make the pliancy of the membrane smooth when the valve opens and closes. Another function of these elastic struts is to hold the membrane in the expanded shape in order to get a good sealing of the valve edges against the inner wall of the lumen. This sealing is also improved by the pressure difference over the valve membrane. In the situation of FIG. 1 the pressure is higher at the concave side of the membrane than on the convex side. Therefor the elastic force of the struts may only be needed to start the opening of the membrane. The elastic behavior of the membrane material itself will also help to open the parachute and cause a good sealing against the wall. In this concept the elastic struts 129 have a preferential unloaded state as drawn in FIG. 1.

The valve will stay in its closed position as long as the pressure difference between the convex and concave side remains negative (higher pressure at the concave side). If such a valve were placed into the aorta to replace the natural heart valve, the apex of the membrane and tip 126 would be placed at the proximal side, while the support stent 121 is placed more distally, for example at the location where the natural heart valve was or is. In the latter case the stent can be used to push the natural valve membrane in the annulus outward and hold the new stented valve there in place at the annulus position in the entrance of the aorta.

Figure 2:
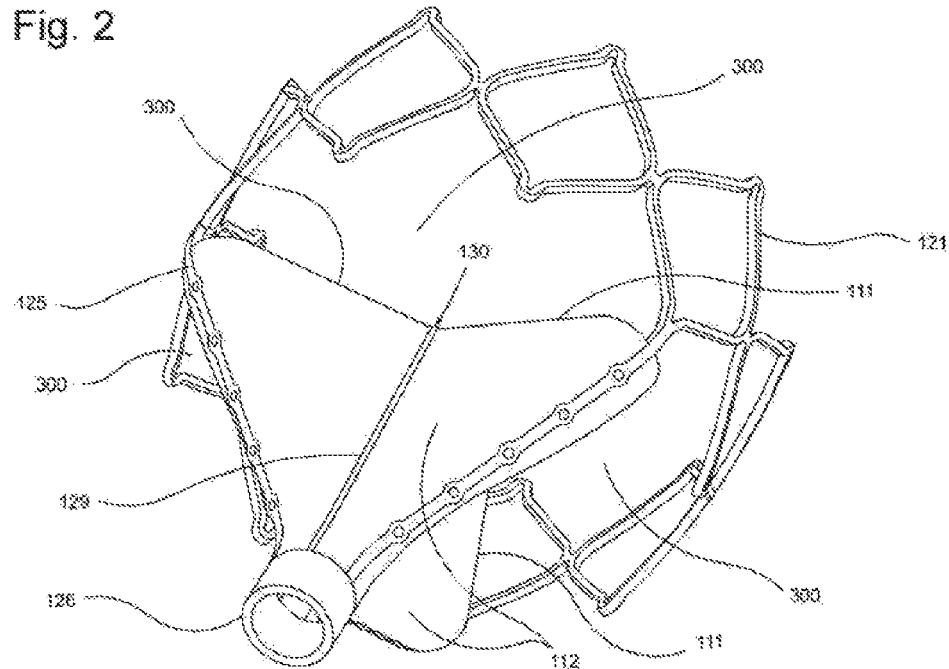
FIG. 2 shows the same device as in FIG. 1, but now the valve membrane is elastically deformed into a shape, which allows the body fluid to pass around the valve and through the stent.

Once the pressure difference becomes positive (higher at the convex side than at the concave side), the blood pressure raise will cause the flexible membrane to collapse into the state as shown in FIG. 2.

In this situation the blood can flow through the three openings 300, which are given free by the deformation of the membrane edges 111. These edges will move away from the stent 121 and thus from the inner wall of the body lumen, and the blood will flow close to the inner wall. This is the major difference with other valves, because the blood now passes around the membrane, instead of passing through it.

It can be seen that the blood pressure has caused a collapse of the three valve leaflets 112, of which two can be seen in FIG. 2. A valve leaflet is held between a set of support struts 125 and connected to tip 126. Elastic struts 129 are now in a deformed state, and will try to expand the valve as soon as the pressure will drop. As can be seen, the valve leaflets 112 have a smooth collapsed shape, caused by the combined forces of blood pressure, elastic behaviour of membrane 110 plus eventual fibers for reinforcement and/or shape control, and by the geometry and elasticity of struts 129 and 125. The necessary elastic outward force, exerted by elastic elements 129 will depend on the type of valve, the natural elasticity of the membrane itself, the reinforcement fibers, the pressure difference and the desirable collapsed profile.

Suppose that the valve of FIGS. 1 and 2 is held in place in an artery, while the blood pressure is higher at the base than at the tip of the cone. In such a case the situation of FIG. 1 occurs. The blood pressure will tend to open the membrane like a parachute, and the edge of the cone base will be pressed against the artery wall. In this position the cone closes the artery and prevents flow.

In FIG. 2 the blood pressure at the tip side is higher than at the base side. Now the surface of the cone will tend to collapse, like a parachute which is held upside down, and the blood flows freely between the membrane and the artery wall. If the pressure difference is alternated repeatedly the cone will jump open and collapse every cycle. This is only possible if the axial position of the membrane is held stable by a supporting structure, like the one of FIGS. 1 and 2.

Tip 126 is a cross section of the tube of which the support frame was fabricated. If the hole is kept open, there will be a certain amount of leakage through this hole, when the blood pressure is higher at the concave side. In the other position, like in FIG. 2, this leakage is not a problem. At that moment the leakage goes into the same direction as the flow around the valve leaflets 112.

There are several options. If the leakage is not too large, it may even be desirable, because it will always flush the inner wall of the valve membrane and keep it clean. There are no "dead zones", where the blood stands still for more than about one second. This will prevent contamination of the valve membrane. Eventual the surfaces of membrane and frame may be coated with a biocompatible coating and a drug releasing layer to improve its characteristics and prevent problems over time.

The second option would be to make the hole in tip 126 smaller by choosing to fill it partly or completely with a stop or close it with the polymer during the dipping procedure.

Another option would be to mount an additional miniature one-way valve inside tip 126. This valve should then open into the same direction as the surrounding valve membrane. Flushing of the inner surface of the valve membrane is so maintained, while the leakage is stopped. Such a one-way valve can even be constructed so, that it is possible to mount the complete device on a delivery catheter, which has an elongated tip that runs through the tip 126. The tip valve is then pushed open by the catheter tip, but after placement it will elastically return to its working position.

Figure 3:
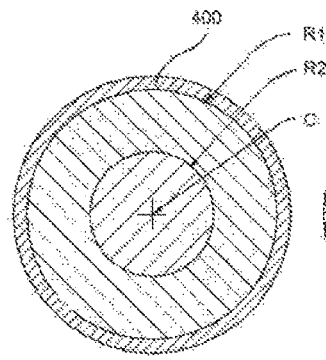
FIG. 3 shows a schematically cross section of a cylindrical lumen.

In FIG. 3 a schematic cross section of a body lumen 400 is given, which has an inner radius R1. Another circle with radius R2 is concentric with the body lumen 400, which has half the diameter of the lumen inner diameter. In general, suppose that a conventional valve opens from the center C, while the flaps are moving outside from C into the direction of the lumen wall. If the thickness of all used materials were extremely small, the flaps could move over R1 and completely open the artery. However the cross section that allows blood flow is determined by the total surface area that the cross section of the support frame, inside layer covering the support structure plus valve flaps occupy. Conventional valves, like the one disclosed in U.S. 2003/0114913, which allows flow through the center, have substantial material thickness and the movement of the flaps is limited. Suppose a simplified model of such a valve, and that the open valve has a circular opening and that in an open state the valve flap tips move from the center over a maximum distance of half the body lumen radius R1. They would than give only a circular area with half the body lumen radius R1 free. In such a case only 25% of the total surface area of the body lumen is then open.

However, this means that 75% of the surface area is not available for blood flow. It would therefore be better to use a valve, which does not open in the center, but instead of that allows the blood to flow around it. With the same movement of the valve flap tips over half the radius, but now with flaps moving from the body lumen wall inward until they reach the circle with radius R2, the effective surface area becomes 75% instead of 25%. Therefore it is better to design valves that allow the body fluid to flow around them instead of through them. In many cases the movement of the valve edges is limited, because for example fatigue may cause problems at large displacements, or because of the material thickness. In such cases the valve model according to this disclosure with flow along the wall, will give more flow than in models with the same valve edge displacement with flow through the center.

FIGS. 4*a*-*d* gives examples of flexible valve membranes in side view, with the length axis vertical. In FIG. 4*a* a conical shape is shown, which can be attached to the supporting frame of FIG. 1 by means of dipping, stitching, gluing or any other well-known technique. The supporting struts may be located at the outside or inside surface of the membrane, or be integrated in the membrane itself. The base of the cone has a diameter that equals the inside diameter of the body lumen. The top of the cone is cut away at the place, where attachment to the tip of the support frame of FIGS. 1 and 2 takes place.

In FIG. 4*b* the valve membrane is locally given a curved surface, like in FIGS. 1 and 2.

FIG. 4*c* shows a valve membrane with edges that are bulged to achieve a better adaptability of the sealing edges against the artery wall. If for example the inner diameter of the body lumen is not very constant, or if the cross section is irregular, the protuberant edge of the membrane may be more forgiving than a straight edge and thus ensure a better valve closure.

Finally, in FIG. 4*d* the membrane surface is made non-conical. It will depend on the type of use, the expected pressures, the used materials and the (variation in) lumen wall geometry, which shape the membrane surface and edges must have.

Figure 5:
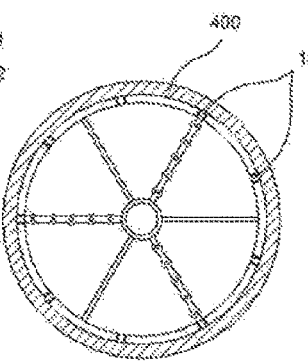
FIG. 5 gives a view in axial direction, showing the valve in its closed position.

FIG. 5 shows a schematically view of the valve in axial direction, showing the concave side of the valve in its closed position, while it is placed inside a body lumen 400. Membrane edges are pushed against the inner wall of the lumen. Dependent on the embodiment that is chosen, the membrane edge may also be pushed against the inner wall of the stent 121. There may also be an additional covering (not shown) of the inside of the stent to improve the sealing against the membrane edge. However, if a side lumen is located near the site where the stent is placed, such a covering of the stent may close the entrance of such a lumen, if the stent is not properly placed. The construction with an open stent wall allows the placement at such locations and is claimed here as an advantage over conventional valves, with membranes attached directly to the stent wall.

Figure 6:
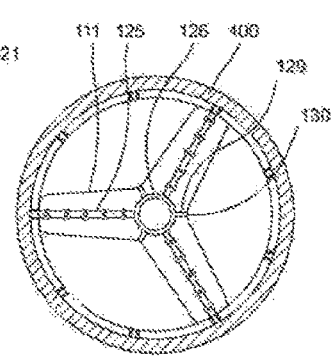
FIG. 6 gives the same view as FIG. 5, but now with the valve in open state.

FIG. 6 gives the same view as FIG. 5, but now with the valve in open state. It is clear that struts 125 support the membrane edges 111. End points 130 of elastic struts 129 are pushed inward by the blood pressure. As soon as the blood pressure drops and is caused to become higher at the concave side, the elastic struts 129 will start moving outside. This movement is helped by the elasticity of the membrane and the parachute deployment effect when the blood pressure rises at the concave side.

Therefore the elastic struts 129 may not be needed in specific stents and become optional. For some applications the device may have to be removable and it has to be possible to collapse it again. If the membrane does not fold up easily it may be difficult to pull the device into a retrieval catheter. In such cases struts 129 may help with the collapse of the membrane to the position as shown in FIG. 2, if the elastic struts 129 have the tendency to spring back to the position parallel to the length axis. Then the collapsing frame cells will enclose and collapse the membrane edge 111, if this edge is located within the circular ring, formed by the cells. Optionally an additional elastic thin skin or skirt may be mounted around the frame cells in order to make the device collapse smoothly without parts of membrane edge 111 protruding through the cell openings.

FIG. 7 shows the device 100 while it is mounted on a delivery catheter 700. The delivery catheter has a distal end section 701 and a distal tip 702, which extend beyond the valve device 100. The delivery catheter also has a short balloon section 710, located inside stent section 121, which has been crimped onto it. For clarity the stent 121 is schematically drawn as a zigzag-line to make the balloon visible in the figure.

Distally from the balloon section 710 the shaft 703 runs through the collapsed membrane 110 and support struts 125. Catheter shaft 703 also runs through ring 126 and ends into the distal tip section 701, which may be steerable.

In FIG. 7 can be seen that inflation of the balloon 710 will exert a radial outward force onto the stent ring 121, but not on the membrane 110. Struts 125 will follow the expansion of the stent ring 121, because they are attached firmly to them. Until delivery the optional elastic struts 129, having the tendency to spread the membrane open, will have to be held collapsed, for example by means of a surrounding seal, which breaks away as soon as the balloon is inflated.

Using a self-expanding material can make an alternative type of support frame. Such a frame is not expanded by means of a balloon like in FIG. 7, but it may be necessary to post-dilate the self-expanding stent in order to reach the optimal diameter for the valve. In addition to the balloon of FIG. 7, a surrounding delivery sheath will be needed to keep the stent 121 in its collapsed state while the device is maneuvered into place. Finally the sheath can be withdrawn and the stent is allowed to expand, eventually followed by the optional post-dilatation by the balloon.

Figure 8B:
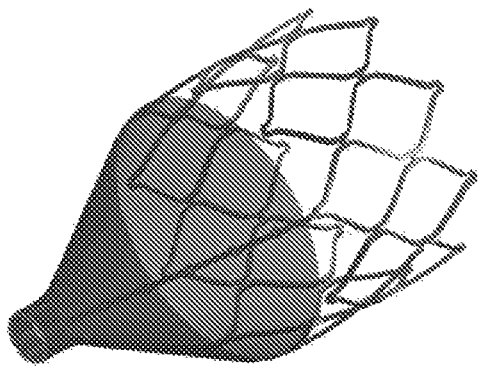
FIGS. 8a and 8b show the stent and valve of FIGS. 1 and 2 in open and closed state respectively, with the valve membrane shown in gray. Now the stent has a double row of unit cells.
Figure 8A:
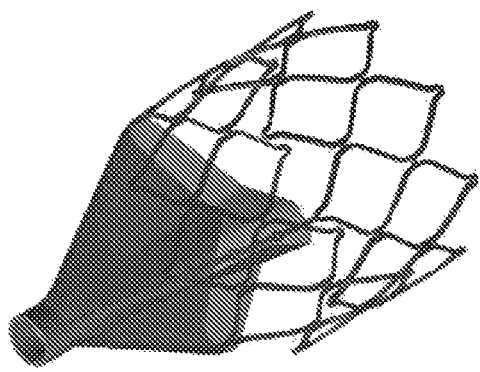

FIGS. 8*a* and 8*b* show the valve of FIGS. 1 and 2 in open and closed state respectively. The frame now has a double row of unit cells. If the total length of valve and frame is a problem because of limited available space, another embodiment as shown in FIGS. 9*a* and 9*b* may be used.

Figure 9B:
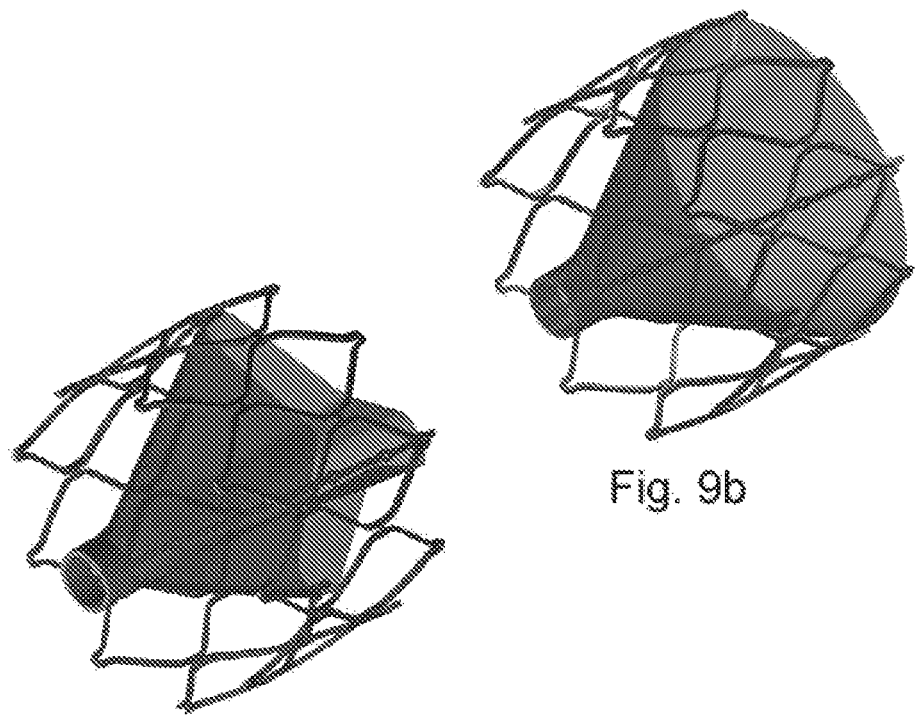
FIGS. 9a and 9b show a shorter assembly of a frame and valve with inverted valve support struts in open and closed state respectively.
Figure 9A:
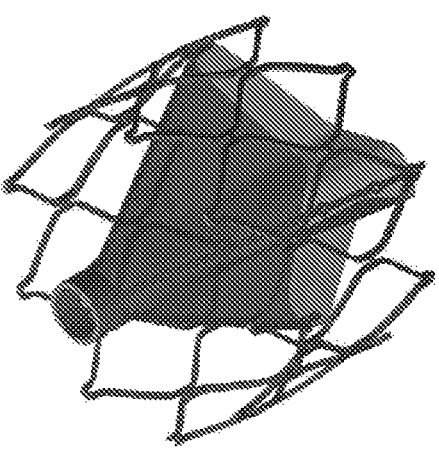

The valve in FIGS. 9*a* and 9*b* is now located inside an inverted stent frame in order to reduce the overall length. The three struts that hold the valve in place are connected to the other side of the frame as compared to the example of FIG. 8. This connection can be by crimping, welding, gluing or any other available technique. Crimping can for example be combined with the use of radio-opaque marker rings. Another option is that three long struts of the frame material itself are bent in such a way that they flip inside the frame in a reverse direction until they form an inverted cone and then connected at the tip of the cone. However, this leads to the disadvantage of having more material at one cross section as compared to the example of FIG. 8.

Pumping Function

In patent U.S. Pat. No. 5,885,258 and related patents U.S. Pat. Nos. 6,780,175, 7,037,321 and 8,052,670 the present inventor has described a miniature balloon pump with a balloon and two one way valves mounted on a single catheter. The balloon is located inside a collapsible self-expanding Nitinol frame. Intermittent changing the volume of the balloon causes a unidirectional flow of fluid. In this patent the balloon volume is changed by mechanical means, instead of present balloon pumps. Other embodiment of patent U.S. Pat. No. 5,885,258 is that an expandable nitinol basket, made from a single slotted piece of tubing, is used to keep a catheter exactly in the centre of a body lumen. This feature is also important for using in balloon pumps.

Conventional balloon pumps are used in cardiac assist devices. The balloon is placed in the aorta and stay by means of a catheter tube in connection with an apparatus that is located outside of the patient's body. The apparatus is controlled in such a way that it can inflate and deflate the balloon with a frequency that is similar to the heart-beating rate. However, the timing of the inflation is very critical, because the aorta should be closed only for a short time starting at the end of the contraction of the left ventricle and during the diastole. This will help improve the flow of blood into the coronary arteries during diastole. The balloon is merely used as a remote controlled occluder and the pumping function is not very efficient as the flow is not directed and the energy is absorbed by the vessel wall. In principle the blood flow caused by the balloon is bi-directional. When two one-way valves are combined with such a balloon and placed in the aorta, it will work not only as a remote controlled occluder, but also as an active pump that helps to increase the total blood flow by directing the blood flow distally, so it becomes more unidirectional.

Figure 10:
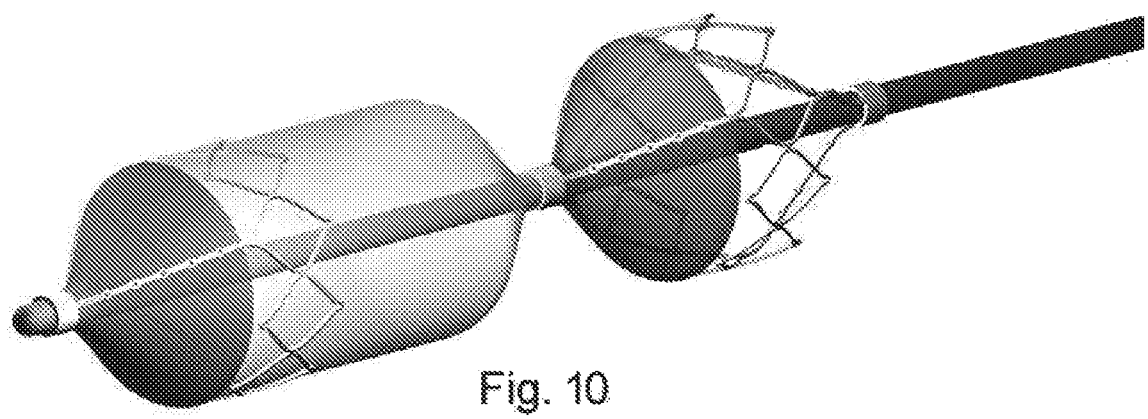
FIG. 10 is a schematic drawing of a balloon pump with two one-way valves.

In FIG. 10 a schematic drawing of such an embodiment is given. The left valve is located proximal and the right valve is distally, seen from the heart valve. In one form as shown, two valves are mounted to relatively short expandable frames and connected to a common flexible catheter. Between the valves a balloon (shown in lighter gray than the two valves) is mounted onto the catheter as well, and this balloon can be inflated and deflated through side holes in the catheter wall. The medium for inflation can be a liquid or a gas, but preferably a gas like helium in order to achieve a high speed in deflation and inflation. When the balloon is in its deflated state, both valves will automatically open when the blood pressure near the heart valve is high enough and the blood flows to the right. In the opposite direction the valves automatically close, like described in the previous figures.

In order to achieve a similar counterpulsation effect as for balloon pumps, the balloon should be inflated to first close the proximal valve by pushing the valve leaflets outside and against the wall. This improves the blood flow into the coronary arteries. Preferably, the most left section of the balloon, which in this figure makes a direct contact with the valve leaflets, inflates faster than the remainder of the balloon to the right. Upon increasing the inflation to the right, a peristaltic movement pushes the blood towards and through the distal valve and into the lower aorta. When the balloon is deflated, preferably rapidly by creating an underpressure through the catheter tube, the distal valve will close and the proximal valve opens in order to fill the space between the aorta wall and the outer surface of the balloon. Such a system can cooperate with the heart in order to improve the coronary blood flow and also increase the total blood output per heartbeat. In fact the device works in series with the heart. Influencing the speed and degree of valve opening and closing will optimize the efficacy of pumping and counter pulsation, and the effective uni-directional flow during diastole may be 2-4 times higher than without using valves. Also the afterload reduction with valves is better than without valves. The total flow depends on the size of the balloon and the driver settings for the pumping frequency, but the better flow output with valves enables the downsizing of the present balloon, which is an advantage. The flow direction can also be influenced by the way of insertion of the system, either through the subclavia or femoral artery.

Figure 11A:
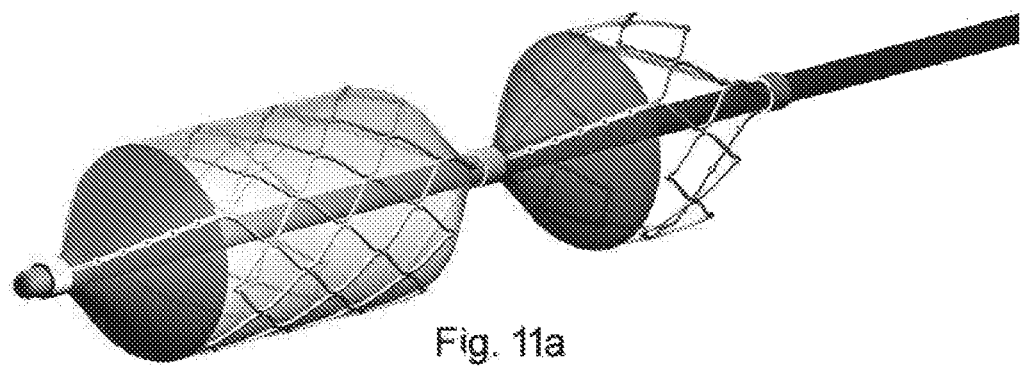
FIG. 11a-c shows other embodiments of a balloon pump, with the balloon placed inside the elongated stent frame section and with direct mechanical interaction between the balloon and the proximal valve.

In FIG. 11a another embodiment is shown, with the balloon placed inside the elongated support frame section. Here the stent frame entirely surrounds the balloon, and in this example the balloon can also close the valve leaflets of the proximal valve, by direct pushing them outside. The distal valve may be located further away and has also its own stent frame, like in FIG. 10. Another option is that the distal stented valve of FIGS. 10 and 11a is of the inverted type as shown in FIGS. 9a and 9b.

Figure 11B:
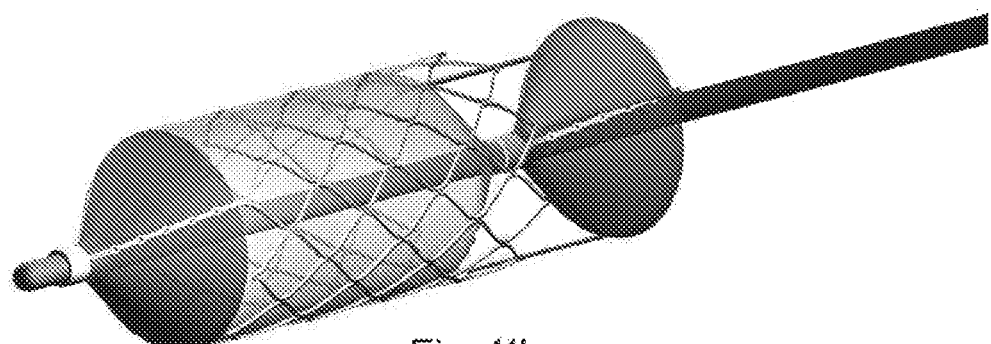
Figure 11C:

FIGS. 11b and 11c give two views of another embodiment, where the distal valve does not have its own expandable frame. The three support struts of the right valve are connected to three elongated struts that are part of the stent frame. The connection can be made by any mechanical means, including gluing, crimping or welding. Another option is that the three valve support struts are cut into the same tubing as the remainder of the frame, than inverted and finally joined at the cone tip. In the embodiments of FIGS. 11a-c the surrounding stent frame may be covered with a pliable, soft polymer sheath layer that protects the aortic inner wall from damage by the movements of the balloon and/or the stent frame. In fact the entire combination of balloon, stent, valve frames and protective sheath can be seen as a complete insertable temporary heart assist device, which can take over or help the heart pumping function.

Figure 12A:
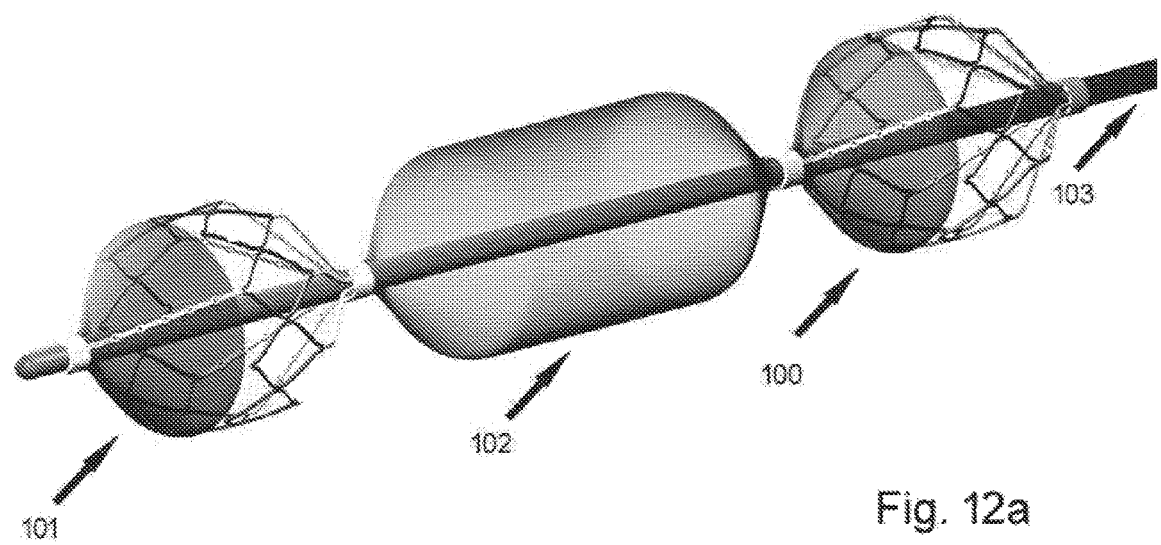
FIG. 12a shows another embodiment where both valves and the balloon are located on the common catheter further away from each other.
Figure 12B:
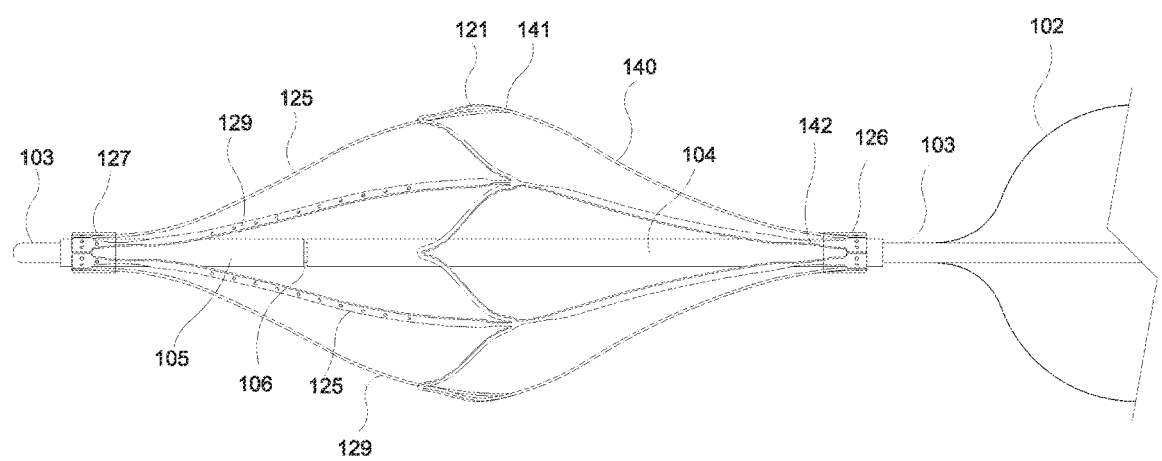

FIG. 12a shows another embodiment where both valves 100 and 101 and the balloon 102 are located on common catheter 103 further away from each other. There is no direct mechanical contact between the valves and the balloon, so the valves open and close in the natural way, dependent on their elasticity and the pressure difference on both sides of the leaflets. If the device has to be retrievable, the construction of the valve frames must enable an easy collapse of the frame plus valve by withdrawal into a sheath. This sheath can be advanced over the catheter 103, in FIG. 12a in the direction from right to left, whereby first the retrieval struts, followed by the 9 cells and finally entire valve 100 is retrieved, then balloon 102 and finally valve 101. Delivery into the aorta is in the reverse direction. The left valve frame 101 of FIG. 12a and a part of balloon 102 are shown in FIG. 12b. The valve frame is basically made of three sections. The middle section is an expandable stent ring, for example in the form of a zigzag ring 121 with a number of unit cells, in this case 6 half cells. Each unit cell is connected to a flexible elongated retrieval strut 140 that is connected to a common ring 126 on the catheter 103, that holds all six struts together by glue or any other means on a short extra tube 104. The connections 142 to ring 126 may have a reduced width in order to make it more flexible, like a hinge. This also counts for the connection points 141 between struts 140 and zigzag ring 121. Similar retrieval struts can be attached to the frames in the previous figures.

Figure 12C:
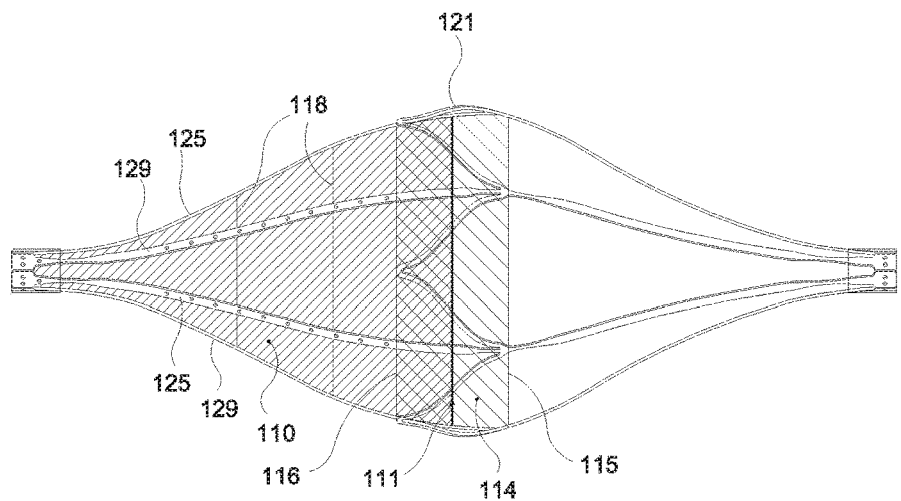
FIG. 12c shows the frame of FIGS. 12a and 12b with the valve membrane mounted on it.

On the left side of valve holder ring 121 three valve holding struts 125 and three free struts 129 are also mounted in a similar way to common ring 127 on catheter short extra tube 105, which slides over catheter 103, while all struts 125 and 129 have their other end connected to ring 121. Expansion and contraction of the frame causes length change, so it is possible when ring 126 is firmly attached to catheter 103, while tube 105 can slide freely back and forth over the catheter surface. Eventually excessive deformation of the frame, if ends 126 and 127 would be pushed too close to each other, can be avoided by choosing the length of tubes 104 and 105 in such a way that their ends meet each other at location 106, thus stopping further expansion. FIG. 12c shows another view on the same frame of FIG. 12b, with valve membrane 110 in the shape of a cone, mounted in the frame with edge 111 located in ring 121. Only three valve holding struts 125 are attached to the valve membrane 110 by glue, stitching or any other means. The three free struts 129 are only used to support the three moving leaflets of the valve membrane and eventually enable a smooth retrieval. This is also the function of the zigzag ring 121, besides its function of supporting the valve structure and holding it in place. During collapse of the device the zigzag struts will squeeze the valve edge 111 to a smaller size, thus enabling sliding everything into the retrieval sheath. Eventually the zigzag ring can be replaced by a ring with full cells, like in FIG. 1 or it may have several cells in length direction as well. Ring 121 may even be constructed from bistable cells.

Another possible embodiment is that ring 121 is surrounded by, or surrounds a flexible elastic skin 114 with edges 115 and 116 that has enough elasticity to follow the expansion and contraction of the ring. In FIG. 12c skin 114 is drawn as an almost cylindrical layer, but in reality it will follow the contour of the zigzag ring. Such a skin can help to prevent parts of the valve membrane edge 111 to protrude through the cell openings, while the frame is delivered or retrieved, when there is sufficient overlap of the edges 116 and 111 of skin and valve membrane. This ensures a smooth collapse of the membrane 110. The membrane 110 can be made of a flexible thin walled polyurethane by dipping on a Teflon cone and it can be reinforced with embedded Keflar or Dyneema fibers 118 to reinforce it in specific directions. Most important is the strength in tangential direction, so fibers 118 are preferably placed around the circumference of the cone. Only two tangential fibers 118 are shown in the figure for clarity, but there can be more, also embedded in other directions. Collapse of the valve edge is also helped by the surrounding unit cells, which will contract and enclose the membrane together with the elastic shrinking of the skin, when the device is retrieved into a sheath.

Figure 12D:
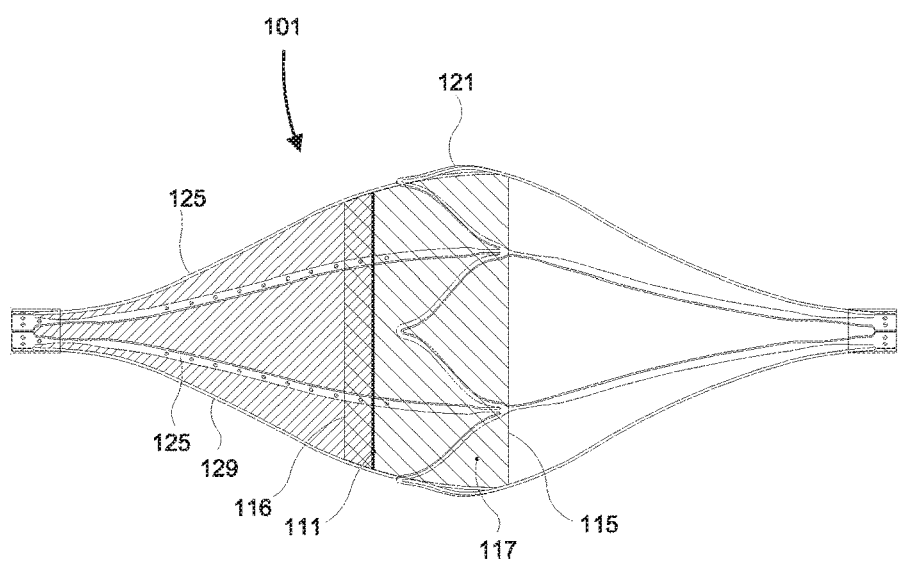
FIG. 12d shows another embodiment of the valve of FIG. 12 a with an additional sealing skirt mounted on it.

FIG. 12d shows a valve almost similar to the one in FIG. 12c, but here the valve cone does not entirely reach the outer diameter of ring 121. Valve edge 111 now rests inside an additional sealing ring that is connected to struts 125 and 129 to form a separate closed ring skirt 117 that reaches onto the inner surface of ring 121. The valve itself works now exactly the same as for the embodiment of FIG. 12c, but at an effective diameter being smaller than the frame 121, which has the same diameter as the aorta or eventually it is slightly smaller. In FIG. 12c the valve edge seals against the aorta or the skin 114, but in FIG. 12d it seals against the ring skirt 117. Skirt 117 and skin 114 may be made of a single construction that does not leave dead zones between ring 121 and valve edge 111 where blood would not be flushed sufficiently. One advantage of using such a skirt with slightly smaller size than the aorta diameter is that the valve membrane does not swipe against the inner wall of the aorta. Further it is possible to give skirt 117 and valve edge 111 exactly the ideal dimensions to ensure good valve performance, while frame 121 takes care of the proper holding and positioning of the device, without having to care if the aorta dimensions and frame dimensions are matching well. This separates the two functions of the construction of frame ring 121 in FIGS. 12b and 12c, where it has to hold the device in place and seal the valve edge. Skirt 117 may be made of a fiber reinforced polymer in order to ensure that it reaches the ideal diameter for sealing performance of the valve membrane edge 111. If there is still some elastic radial expansion force left in the struts of the frame, there will be a final equilibrium state wherein the expansion forces are biased by the tangential reinforcement fibers in the skirt. The same biasing effect can be used in the skin 114 that surrounds the frame ring 121 in order to ensure a predictable and stable final diameter after expansion. Reinforcement fibers can for example be made of fine Dyneema, which has a high flexibility on bending, combined with extremely high tensile strength and Youngs modulus on tension. Alternatively the skin 114 may act as a flexible sealing between frame 121 and the aorta wall.

Other combinations of balloons and valves can be made as well. For example a valve located between two balloons on the same catheter may cause a better, more stable positioning of the valve in the lumen. The sizes of such balloons may be different from each other, dependent on the body location, where they are used. Eventually additional frames without valves can be used to keep the balloons centered in the lumen in order to avoid energy loss and whipping of the balloon against the inner wall and/or cause a more stable anchoring to avoid longitudinal movements.

While using balloon pumps with valves, instead of a balloon pump without valves, the flow away from the heart is improved and directed better, but it is not always necessary to have full closure of the valves. In many cases it is better to still have some leakage through or around the valve, for example to create a sufficient counter-pulsation for the blood supply into the coronary arteries.

Therefore, the dimensions and geometry of the valve membrane have to be optimized for the specific use. Intended leakage may also cause better flushing of the valve membrane, thus keeping it clean over time.

The conical valve construction in an expandable frame has a very low delivery profile, and it can also easily be withdrawn into a retrieval catheter, together with the balloon.

Inflatable Valve Leaflets

Instead of using a separate balloon for closing the valve by pushing the leaflets to the artery wall, another type of valve is hereby given in FIGS. 13a and 13b. The volume of the balloon in FIGS. 10-12 is needed for the pumping function. However, if for different applications only a short remote controlled closure of the valve is needed, the inflation and deflation of the relatively large balloon is too slow. The device shown in FIG. 13a-b is an expandable frame and a valve with two conical valve membranes with a common sealed outer edge at the base, both mounted on the same catheter. The two cones have a different top angle and therefore there is an intermediate hollow room in between. There are one or more side holes in the catheter section that is in between the two cone tips, and this makes it possible to inflate or deflate the valve itself. Without any internal pressure both cones act similar to the valves earlier described in FIGS. 1-12. Similar to the examples shown in FIGS. 2 and 6, the common edges at the base of the cones can fold inside and outside. When the valve should be closed actively, the pressure in the intermediate room is raised and both cones change shape and this combination becomes stiffer. It now pushes tight against the artery wall, independent of the external pressure difference of the blood on both sides. It is clear that the volume of the inflation medium that is needed to close the valve is only a fraction of the volume needed for a much larger balloon, so the speed of inflation and deflation can be much higher. Further the size of the catheter lumen can be smaller than for a balloon pump. Such a remote controlled valve closure enables active flow control, independent of the systolic and diastolic pressure variations that cause the movements of passive valves. If the valve is not inflated, it will work as a normal one-way valve.

In order to make such a valve retrievable additional struts can be attached to the right end of the expandable ring, like in the examples of FIGS. 12a-d.

The example given in FIGS. 13a and 13b is only one embodiment of a valve that can be remotely closed by inflation of the valve leaflets. It may be clear that different configurations of such remote controlled valve membranes with inflatable chambers are also meant to be included in the principle of the disclosure.

Reinforced Membranes and Filters

The present inventor has also described expandable frames holding reinforced membranes in patent application PCT/IB2003/004070 . By embedding high strength fibers the membranes may be reinforced in order to improve the reliability of these membranes.

In WO2004/026175 many embodiments for reinforced membranes are claimed, including perforated filters, but also unperforated reinforced membranes for valves and balloons. All these embodiments are to be meant as claimed for the use in combination of devices according to the present disclosure.

Another type of support frame may be made by means of a stent with bistable characteristics. Such a stent can be of a balloon triggerable self-expanding type. The same inventor in PCT/US98/01310 claimed details of such stents and it will be clear to those skilled in the art that such bistable stents are ideal in some cases to support valves in body lumens. Most important feature of stents based on the bistable technology is the increasing radial strength for increasing diameter. This is opposite to conventional stents which have a positive spring rate, resulting in a collapsed state where the forces (and thus friction in the delivery tube) are high, while they get lower upon expansion. Self-expanding stents with bistable design have a negative spring rate, low holding force in the delivery tube and high radial strength after expansion. This gives the stent frame a predictable, well controlled final diameter and a very strong supporting platform for the valve membrane.

One more type of stent frames is of the balloon expandable, light curing type. Such a stent frame can also be provided with a valve according to this disclosure.

Although in the examples of this disclosure merely the application as a stent-supported aorta-valve was mentioned, it is an object of the disclosure that any other embodiment, making use of the same function, can be used.

Examples of such valves are not only short valves in fluid environments like veins, arteries, urinary ducts, sphincters or the like, but also for valves, integrated in longer stents. The medium does not per se have to be a liquid, but can also be highly viscous or eventual low viscous, like air or other gaseous medium.

Also at locations where unidirectional occlusion is desirable, such valves can be used. One example is a pressure relief valve, used to only open if a critical pressure is exceeded. In such cases the membrane valve may have to be pressed against the lumen wall with a higher force than in the case of a heart valve. The closure pressure of such a pressure relief valve may not be caused by additional pressure from the concave side, so the membrane itself has to be stronger than in the case of a heart valve, which is actively and alternatingly moved by hydraulic pressure from two sides.

Valve With Double Frame

When a patient needs a new valve, the original valve is in many cases heavily calcified and it is necessary to prepare the annulus by valvuloplasty in such a way, that there is enough room to place the new stented valve. However, it may be difficult or even impossible to create a smooth and circular cross section with the right diameter in the location of the annulus where the valve comes. This may cause problems, because the valve leaflets may not close perfectly when they have to function in a non-circular housing of the wrong dimensions. Although the material of which the valve leaflets are made is made very flexible, it will also give other complications, like a poor flow pattern and reduced fatigue behaviour. The latter may be caused when the valve is overstretched beyond its nominal size in order to try to close the gap between annulus and outer surface of the stented valve frame. From this moment on the valve leaflets are in fact just too short to work properly. For example, a 24 mm valve works well at a nice round 24 mm end size, but not if it is placed in an annulus of 25 or 26 mm diameter and it may be even worse if the end shape is non-circular.

It is of great importance to assure that the valve frame has its ideal diameter and that it has a perfectly circular cross section where the valve is mounted.

There can be several reasons for leakage through or around an implanted valve. First it can be regurgitation through the interior of the valve, caused by a poor closure of the valve leaflets. If the leaflets are allowed to take their ideal position and shape it may be expected that a well designed and produced artificial valve has no or almost no regurgitation. This ideal shape and position may not always remain the same, as the shape and dimensions of the annulus may change over time, which eventually leads to the need of a replacement of the valve or placement of a second artificial valve inside the first one. The latter is called a "valve-in-valve" procedure. It may be clear that such a second operation is far from ideal.

Another potential risk of creating leakage through the valve can be the formation of new stenosis-like deposits on the surface of the leaflets, because the flow pattern is not ideal if the geometry and size of the artificial valve does not meet the ideal situation.

There is not only leakage through the valve. A major issue is paravalvular leakage between annulus and the stent frame that holds the valve in place. Many solutions have been proposed, using a skirt wrapped around or sewed to the stent frame, but they only work well when the stent frame pushes itself tight enough to the annulus wall. Therefor the stent frame has to adapt to the local geometry and dimensions of the annulus and full closure of the gap may be reached, at least initially. However, over time the annulus shape and geometry may change again and paravalvular leakage may start again in a later period. Even worse problems may be caused by the fact that by adapting the outer dimensions of the outer surface of the stent frame to the annulus in order to prevent outer leakage automatically leads to a deviation of the inner stent frame surface from its ideal shape, resulting in leakage through the leaflets. Placing an artificial valve with a single stent frame will almost always lead to a compromise between acceptable values for leakage through and around the valve. It is very difficult to choose the proper stent size that meets both requirements at once.

The present disclosure proposes the solution for the problems summarized above, by separating the functions of holding the valve leaves in their ideal shape and dimensions and mounting the device without paravalvular leakage in the annulus, even if the geometry and size of the annulus change over time. This can be realized by using two more or less concentric expandable frame sections, mounted together in such a way that the inner frame is holding the valve, while the outer frame has the dimensions and radial force that is needed to keep the device fixed properly in the annulus.

FIGS. 14a and 14b show such a valve, built into a double frame. FIG. 14a gives a side view of such an aortic valve 150, built into the annulus 151, while FIG. 14b shows a cross section of the same, but now in the open state and with the annulus left away for clarity.

The outer frame comprises a more or less cylindrical middle section 152 and eventually also two flared sections upstream and downstream to provide a smooth anchoring in the anatomy of the annulus, the ventricle exit and the sinuses of the adjacent ascending aorta, respectively schematically depicted as 153 and 154. The flared section 154 may have a three-lobed shape to fit well in the sinuses, as shown in FIG. 14b. The inner valve holder frame 121, holds the three valve support struts 125, similar to the ones described before and has the ideal dimensions for a perfect behavior of the valve membrane 110, and its geometry is independent of the variations in geometry of the annulus. Optionally the cells of frame 121 are covered with skin 114 or 117, like in the previous FIGS. 12c and 12d. Between the inner and outer frame sections a flexible adaptive skirt 155 seals the gap in order to prevent paravalvular leaking. Such a skirt can be flexible enough to adapt to already existing or future geometry variations between inner and outer frame, so an eventual non-circularity of the annulus, as shown in FIG. 14b, is not transferred mechanically to the leaflets. Of course it is ideal to have the gap between inner and outer frame as small as possible, so precise imaging of the geometry of the annulus and the choice of the best combination of the two frames is crucial. The sealing function of skirt 155 works in two directions, preventing leakage in axial direction as well as radial. Skirt 155 may swell or wrinkle outside through well.

Skirt 155 seals against axial leakage and further closes the radial gap between the frames, but can also be used to cover the frame surfaces, where this is needed. All materials that are presently used for sealing valve frames or for making grafts may be suitable for this purpose, including fiber reinforced composite materials. For example a fiber reinforced membrane would do. Another possible skirt material would be swellable when it absorbs fluid in order to provide better sealing. Still another skirt material wrinkles upon shortening of the outer frame when it is placed, causing an increase in wall thickness locally. The skirt 155 also can protrude through the openings in the unit cells of the outer frame 152 in order to seal against the annulus around the outer frame. Additional skirt material can be applied to the outer surface of the outer frame.

The inner and outer frame may be made of one single piece of tubing, but can also be made of two separate sections, which are later mounted together. The materials and designs for the inner and outer frame may be identical, but can be different as well, including a different elastic behavior. While the outer frame may be balloon expandable, like in the Edwards Sapien valve, or self-expandable like in the Medtronic Corevalve, or a lockable woven mesh structure like in the Boston Scientific Lotus valve, the inner frame may be of a different type. One example for the inner frame would be a self-expanding bistable stent type as described in patent U.S. Pat. No. 6,488,702 by the present inventor. Such a stent frame can have a negative spring rate, ensuring that it will expand with an increasing force which is optimal at its final expanded diameter. Such a stent frame can be held in a delivery sheath with relative low radial force, but once it comes out of the sheath and starts expanding, it becomes stronger and stronger, the further it expands. This expansion will stop as soon as the stent frame reaches its planned final diameter, where it reaches the ideal size and shape to be the perfect housing for the valve. Another option is for the inner frame to use a bistable balloon triggerable stent, which also has a well-known and very stable final geometry. Of course any other combination for inner and outer frame can be made as well, without leaving from the spirit of the present disclosure. The connection between outer and inner frame may be by means of metal struts running between the two surfaces of the frames, or by additional crimped connecting markers, or only by the skirt material itself.

The sealing material that prevents the radial leaking through the stent openings may be identical to the skirt material that prevents the leakage in axial direction between annulus and outer frame, or between outer frame and inner frame. In another option these materials are different, because their function is different. The skirt material must be able to take up relative large gap variations because of eventual non-circularity of the outer frame as compared to the circular inner frame. The skirt material does not only have to be mounted between inner and outer frame in radial direction, but may also have sections with a more tapered shape for causing a better flow pattern of the blood and preventing the existence of dead zones where the blood would stand still without being flushed at every heartbeat. This prevents the local forming and accumulation of clots and calcification.

As the outer frame has to be placed in the annulus where it has the best grip and support for the native valve tissue, without closing the entrances of the coronary arteries, the inner frame with the valve does not necessary have to be located at the exact same axial location, although this is an option as well. It may be that the inner frame with valve is placed more upstream or more downstream than the annulus as well, without departing from the spirit of the present disclosure. The sealing material on the frame surfaces and the skirt connecting both frames must close the gaps in radial as well as axial direction then.

The conical valve, as described and shown in FIGS. 1-9, is just one of the possible options to use in the inner frame. Conventional valve structures with one, two, three or any other number of leaflets and a central opening can be mounted in the double frame stent as well and also will work better as long as the geometry and size of the inner frame are ideal.

Such valve systems can not only be used for replacing the aortic valve, but also on other places, where the geometry and stability of the surrounding tissue is not ideal for placing a conventional stented valve.

Optionally, the outer frame is placed first and the inner frame with valve is placed separately thereafter. The method of attachment of the inner frame to the outer frame is more difficult then, but it opens the way to replacing an inner frame after time, while the outer frame stays in place. Also, the sealing by the skirt between the frames needs to be very reliable and it is easier to make and prepare the double frame device entirely as a single device. However, the option of making a customized separate inner frame with a skirt around it, and placing it apart from the outer frame, may be interesting in special occasions.

It is within the scope of the disclosure that any material or any combination of materials can be used in any configuration to build the valves discussed herein.

It will be obvious to those skilled in the art having regard to this disclosure that other modifications of this disclosure beyond these embodiments specifically described here may be made without departing from the spirit of the disclosure. Accordingly, such modifications are considered within the scope of the disclosure as limited solely by the appended claims.

It is noted that terms like "preferably", "generally" and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure Likewise, for the purposes of describing and defining the present disclosure, it is noted that the terms "substantially" and "approximately" and their variants are utilized herein to represent the inherent degree of uncertainty that may be attributed to any quantitative comparison, value, measurement or other representation, as well as to represent the degree by which a quantitative representation may vary without resulting in a change in the basic function of the subject matter at issue.

While certain representative embodiments and details have been shown for purposes of illustrating the disclosure, it will be apparent to those skilled in the art that various changes may be made without departing from the scope of the disclosure, which is defined in the appended claims.

The invention claimed is:

1. A device for a stented prosthetic one way valve for regulating the blood flow in the aorta, comprising:
    a flexible conical membrane with an apex and a base edge;
    a radially expandable valve support frame to hold the conical membrane in place, the valve support frame comprising a tapered section comprising valve holder struts that hold at one end the conical membrane to the apex and at the other end to a substantially cylindrical section of the valve support frame that is made from an arrangement of expandable unit cells, wherein a final diameter and shape of the valve support frame after expansion creates an optimized fit for the closure of the base edge, whereby the conical membrane can collapse in order to allow blood flow between it and an inner wall defined by the valve support frame;
    a skin that surrounds or is surrounded by the valve support frame, the skin comprising a plurality of reinforcing fibers such that a final diameter of the skin after expansion is limited and defined by the length of the fibers that extend along a tangential direction of the skin;
    an outer annulus holder frame shaped to adapt to an annulus anatomy and which holds the valve support frame in place; and
    an adaptive sealing skirt that prevents paravalvular leakage between both frames in axial and radial directions.

2. The device of claim 1, the position of the attachment of the valve holder struts of the tapered section to the valve support frame being located at the inflow end, the outflow end or somewhere in between both ends of the valve support frame.

3. The device of claim 1, wherein delivery and retrieval are enabled by the relative movement of a catheter with the valve support frame in and out of a surrounding sheath.

4. The device of claim 1, wherein a certain amount of leakage of the valve is further used to flush the apex.

5. The device of claim 4, further comprising a miniature check valve located inside the apex to limit or regulate the amount of leakage.

6. The device of claim 1, wherein the base edge of the conical membrane moves and seals against an inner surface of an additional ring shaped skirt that is mounted on the valve holder struts, wherein the base edge of the conical membrane has a diameter that is smaller than the diameter of the valve support frame.

7. The device of claim 6, wherein the ring-shaped skirt is further attached to the cylindrical section of the valve support frame, thus configured to close a gap between a wall of an annulus anatomy and an edge of the one way valve in order to prevent paravalvular leakage.

8. The device of claim 1, wherein the outer annulus holder frame has a flared end at the upstream side to prevent migration of the outer annulus holder frame.

9. The device of claim 1, wherein the outer annulus holder frame has a flared end at the downstream side to prevent migration of the outer annulus holder frame.

10. The device of claim 9, wherein the flared end at the downstream side of the annulus holder frame has a three-lobed shape to accommodate to an aortic sinus anatomy.

11. The device of claim 1, wherein the conical membrane is made of any biocompatible polymer, metal, organic tissue, fabric or combinations thereof.

12. The device of claim 1, wherein the conical membrane is reinforced with embedded or connected fibers with enhanced tensile strength and high flexibility on bending.

13. The device of claim 1, wherein the conical membrane is connected to flexible elastic fibers or struts for shape control.

14. The device of claim 1, wherein the unit cells are made of materials including polymers, metal, Nitinol with superelastic, linear elastic, bistable, multistable properties and combinations thereof.

15. The device of claim 1, wherein expansion during placement can be achieved by balloon expansion, self-expansion, balloon triggerable self-expansion, balloon expandable light curing stent surfaces and combinations thereof.

16. The device of claim 1, wherein the shape and number of the valve holder struts supporting the conical membrane and connecting it to the valve support frame is variable, depending of the use of the one way valve.

17. The device of claim 1, wherein the number of unit cells in tangential and axial directions in the valve support frame may be varied, dependent on the place of use within the aorta.

18. The device of claim 1, further comprising hooks configured to hold the device secured in an annulus anatomy.

19. The device of claim 1, further comprising an anti-thrombotic coating and/or additional drugs applied to the surface of at least one of the one way valve and valve support frame.

20. The device of claim 1, wherein the base edge of the conical membrane defines a bulged or protuberant shape.

21. The device of claim 1, wherein the base edge of the conical membrane moves and seals against the inner surface of the fiber-reinforced skin.

* * * * *